United States Patent [19]

Munford et al.

[11] Patent Number: 4,929,604
[45] Date of Patent: May 29, 1990

[54] LIPOPOLYSACCHARIDES OF REDUCED TOXICITY AND THE PRODUCTION THEREOF

[75] Inventors: Robert S. Munford; Catherine L. Hall, both of Dallas, Tex.

[73] Assignee: Board of Regents, The University of Texas System, Austin, Tex.

[21] Appl. No.: 868,428

[22] Filed: May 28, 1986

[51] Int. Cl.$^5$ .................... A61K 31/715; C12P 19/26; C12N 9/16; C07H 13/10
[52] U.S. Cl. ........................................ 514/53; 514/54; 435/84; 435/197; 536/53
[58] Field of Search .................... 435/197, 84; 514/53, 514/54; 536/53

[56] References Cited

U.S. PATENT DOCUMENTS

| | | |
|---|---|---|
| 4,057,685 | 11/1977 | McIntire . |
| 4,148,877 | 4/1979 | Choay et al. . |
| 4,185,090 | 1/1980 | McIntire . |
| 4,242,270 | 12/1980 | Ayme et al. . |
| 4,435,386 | 3/1984 | Ribi et al. . |
| 4,436,727 | 3/1984 | Ribi . |
| 4,436,728 | 3/1984 | Ribi et al. . |
| 4,505,899 | 3/1985 | Ribi et al. . |
| 4,505,900 | 3/1985 | Ribi et al. . |
| 4,677,194 | 6/1987 | Hao .................................... 530/350 |

OTHER PUBLICATIONS

Ribi, E. et al., (1982) Cancer Immunol. Immunother. 12, 91–96.
Takayama, K. et al., (1981), Cancer Res. 41, 2654–2657.
Qureshi, N. et al., (1982), J. Biol. Chem. 257 (19), 11808–11815.
Kotani et al., (1985), *Infect. Immun.*, 49:225–237.
Tacata et al. (1985), *Infect. Immun.*, 48:219–227.
Homma et al. (1985), *J. Biochem.*, 98:395.
Galanos et al. (1984), *Eur. J. Biochem.*, 140:221–227.
Hall and Munford (1983), *Proc. Natl. Acad. Sci. U.S.A.*, 80:6671–6675.
Rosner et al. (1979), *J. Biol. Chem.*, 254:5926–5933.
Gimber and Rafter (1969), *Arch. Biochem. Biophys.*, 135:14–20.
Munford and Hall (1985), *Infect. Immun.*, 48:464–473.
Vernet (1984), *Rev. Inf. Dis.*, 6:452–454.
Freudenberg et al. (1984), *Rev. Inf. Dis.*, 6:483–487.
Kotani et al. (1984), *Infect. Immun.*, 485:293–296.
Sutherland (1977), "Surface Carbohydrates of the Prokaryotic Cell", pp. 236–239.
Dialog and Lexpat Search of the Scientific and Patent Literature.

*Primary Examiner*—Thomas G. Wiseman
*Assistant Examiner*—Charles L. Patterson, Jr.
*Attorney, Agent, or Firm*—Arnold, White & Durkee

[57] ABSTRACT

An acyloxyacyl hydrolase from the human promyelocyte cell line HL-60 has been found to specifically hydrolyze fatty acids form their ester linkages to hydroxy groups of 3-hydroxyfatty acids, the latter being bound in turn to LPS glycosaminyl residues. The hydrolyzed fatty acids may include dodecanoic acid, tetradecanoic acid and hexadecanoic acid. This enzyme showed a molecular weight between about 50,000 daltons and about 70,000 daltons.

Altered bacterial LPS substantially without fatty acids bound in ester linkage to hydroxy groups of 3-hydroxyfatty acids covalently linked to a glucosaminyl moiety of LPS lipid A are produced. Since the structure of the lipid A moiety is highly conserved, acyloxyacyl hydrolase may act on LPS of many different pathogenic bacteria (for example Salmonella, Escherichia, Hemophilus, and Neisseria).

Such altered bacterial LPS, having toxicity reduced more than immunostimulatory activity, may be therapeutically useful: (1) as vaccines to prevent Gram-negative bacterial diseases by inducing antibodies to LPS 0-polysaccharide or R-core antigens, (2) as antidotes to treat or prevent gram-negative bacterial sepsis ("septic shock"), or (3) as adjuvants to enhance formation of antibodies to other antigens. The acyloxyacyl hydrolase itself may be therapeutically useful to detoxify endogenous LPS in patients with gram-negative bacterial diseases or to remove toxic LPS from therapeutic injectants.

14 Claims, 3 Drawing Sheets

LIPOPOLYSACCHARIDES OF REDUCED TOXICITY AND THE PRODUCTION THEREOF

The United States Government may have rights in the present invention because the development was partially supported by NIH grant R01 AI18188 from the Department of Health and Human Services.

BACKGROUND OF THE INVENTION

The present invention relates to the detoxification of bacterial endotoxin (lipopolysaccharide) by enzymatic modification of its lipid A moiety. The prophylactic and therapeutic use of such detoxified endotoxins is also a subject of the present invention.

Animals mount a complex array of inflammatory responses to tissue invasion by gram-negative bacteria. Many of these responses appear to be provoked by the lipopolysaccharides (LPS) that are present in the bacterial outer membrane. Much evidence suggests that the lipid A region of LPS directly stimulates host cells such as macrophages, neutrophils, and endothelial cells, which then mediate the inflammatory changes. Responses to LPS may be toxic (hypotension, coagulation disturbances, death) or beneficial to the infected host (enhancement of antibody formation, mobilization of phagocytes, acute phase protein synthesis, others).

Typical gram-negative bacterial lipopolysaccharides (LPS) have 3 major structural regions: the O polysaccharide, the R-core oligosaccharide, and lipid A (FIG. 1 and FIG. 2). The structure of the O polysaccharide is highly variable between organisms, even in the same species, and its antigenicity serves as a basis for serotyping the bacteria. The R region is a bridge between the O-antigen and lipid A; its structure is similar in most gram-negative bacteria. Antibodies to LPS (typically directed to O- or R-core antigenic sites) may promote phagocytosis or killing of the bacteria, or they may enhance removal of LPS from the bloodstream into sites (liver, spleen) where the LPS are degraded. The O-antigen is the most antigenic component of the LPS, yet it has little known toxicity. Lipid A, in contrast, is poorly antigenic but contains the toxic center of the molecule. The lipid A moiety is remarkably similar in structure across a wide range of bacterial genera.

The lipid A of enteric bacteria (e.g. Salmonella, E. coli) is a glucosamine disaccharide that is phosphorylated at positions 1 and 4' and has 6 or 7 covalently-linked fatty acids (FIG. 1). Four molecules of 3-hydroxytetradecanoate (3-OH-14:0) are attached to the glucosamine disaccharide at positions 2, 3, 2', and 3'; the hydroxyl groups of the 3-OH-14:0 residues at positions 2' and 3' (and sometimes 2) are substituted with normal fatty acids (dodecanoate, tetradecanoate, hexadecanoate) to form acyloxyacyl groups. In 1983 the discovery of a novel enzymatic activity was reported. This enzyme was an acyloxyacyl hydrolase, found in the granule fraction of human peripheral blood neutrophils, that selectively removed the nonhydroxylated acyl chains from Salmonella typhimurium LPS (Hall and Munford (1983) Proc. Nat. Acad. Sci. V 80, pp 6671–6675). It was known that Dictyostelium discoideum (slime mold), which utilizes Gram-negative bacteria as a major foodstuff, contains enzymes that remove nonhydroxylated and hydroxylated acyl chains from LPS (Rosner et al. (1979) J. Biol. Chem. V 254, pp 5926–5933). The experiments of Gimber and Rafter (Arch. Biochem. Biophys. (1969), V 135, pp 14–20) had also suggested that deacylation of LPS is carried out by intact neutrophils.

Recent studies of the biological activities of chemically synthesized lipid A analogs and biosynthetic precursors of lipid A ((Galanos et al. (1984) Eur J. Biochem. V 140, p 221; Takada et al. (1985) Infect. & Immun. V 48, p 219; Kotani et al. (1985) Infect. I Immun. V 49, p 225; and Homma et al. (1985) J. Biochem. V 98, p 395)) have provided valuable information about structure-activity relationships. Lipid A analogs that lack nonhydroxylated acyl chains are not reactive in the dermal Shwartzman test and have reduced pyrogenicity, yet they are nearly equipotent with complete lipid A in various assays of immune stimulation (such as B-cell mitogenicity, adjuvanticity, and stimulation of macrophages to release $PGE_2$). The effects of acyloxyacyl hydrolase on the biological activities of LPS are in general agreement with these earlier findings: acyloxyacyl hydrolysis detoxifies LPS without destroying the immunostimulatory activity.

SUMMARY OF THE INVENTION

An acyloxyacyl hydrolase from human neutrophils has been found to specifically hydrolyze fatty acids from their ester linkages to hydroxy groups of 3-hydroxyfatty acids, the latter being bound in turn to LPS glycosaminyl residues. The hydrolyzed fatty acids may include, for example, dodecanoic acid, tetradecanoic acid and hexadecanoic acid. This enzyme, at least partially purified from human promyelocytes, has the above described specificity. Gel chromatography of the purified enzyme preparation showed a molecular weight between about 50,000 daltons and about 70,000 daltons.

Altered bacterial LPS substantially without fatty acids bound in ester linkage to hydroxy groups of 3-hydroxyfatty acids covalently linked to a glucosaminyl moiety of LPS lipid A are produced as described herein. Said altered bacterial LPS characteristically have bound 3-hydroxyfatty acids with hydroxy functions at least substantially unesterified. Since the structure of the lipid A moiety is highly conserved, acyloxyacyl hydrolase may act on LPS of many different pathogenic bacteria (those studied include Salmonella. Escherichia, Hemophilus, and Neisseria).

Such altered bacterial LPS, having toxicity reduced more than immunostimulatory activity, may be therapeutically useful. Such therapeutic usefulness comprises use of the altered LPS (1) as vaccines to prevent gram-negative bacterial diseases by inducing antibodies to O-polysaccharide or R-core antigens, (2) as antidotes to treat or prevent gram-negative bacterial sepsis ("septic shock"), or (3) as adjuvants to enhance formation of antibodies to other antigens. The acyloxyacyl hydrolase itself may be therapeutically useful to detoxify endogenous LPS in patients with gram-negative bacterial diseases.

LPS is a glycolipid that has a saccharide chain covalently attached to a lipid (lipid A). LPS molecules may have different lengths of saccharide chain. The saccharide chain has two regions, O-antigen and R-core as shown. Molecules that contain both O-antigen and R- core are called "smooth," while molecules that have only R-core are called "rough." S-LPS refers to smooth LPS (i.e., containing O-antigen). R-LPS refers to rough LPS. The R-core is further subdivided, according to its length, from Ra (complete core) to Re (only 2-keto-3-deoxy-octulosonic acid (KDO)). The term "deep-rough" LPS refers to Re LPS. SR-LPS have one O-antigen repeat unit attached to the R-core.

Figure 2:
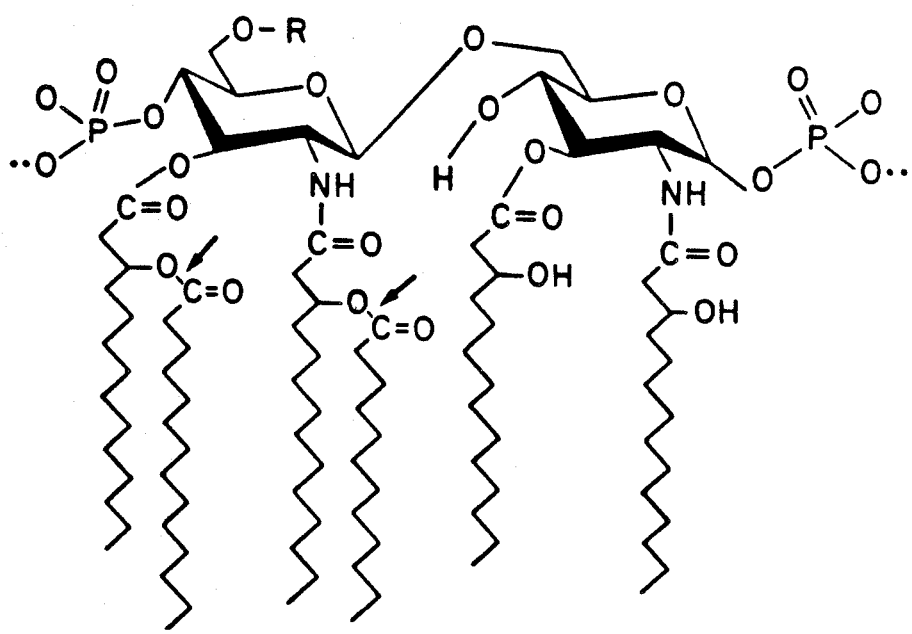

FIG. 2 shows the proposed general structure of enterobacterial lipid A. R=site of attachment of the polysaccharide chain. Arrows indicate the site of action of acyloxyacyl hydrolase.

Figure 3:
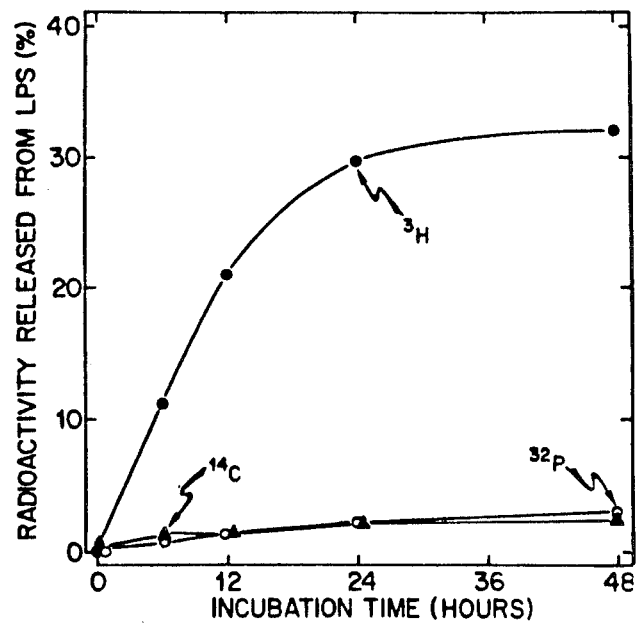

FIG. 3 shows the time course for release of $^3$H-fatty acid, $^{14}$C glucosamine and $^{32}$P phosphate from labeled LPS in the presence of acyloxyacyl hydrolase.

Figure 4:

FIG. 4 shows the effects of deacylation upon labeled LPS samples subjected to electrophoresis in polyacrylamide gel with sodium dodecyl sulfate. Each lane contained 0.5 ug LPS. The gel was treated with En$^3$Hance (New England Nuclear) and exposed to Kodak X-Omat XAR-5 film at $-70°$ C. Lane 1 contained S-LPS (about 1% deacylated); lane 2, S-LPS (25% deacylated); lane 3, SR-LPS (0.6% deacylated); lane 4, SR-LPS (15%); lane 5, SR-LPS (28%); lane 6, SR-LPS (65% deacylated with NaOH); lane 7, Rc-LPS (1%); lane 8, Rc-LPS (20%); lane 9, Rc-LPS (32%); lane 10, Rc-LPS (65% deacylated with NaOH); and lane 11, S-LPS (1%). The LPS in lanes 6 and 10 were deacylated by treatment with NaOH, which hydolyzed all ester bonds.

Figure 5:
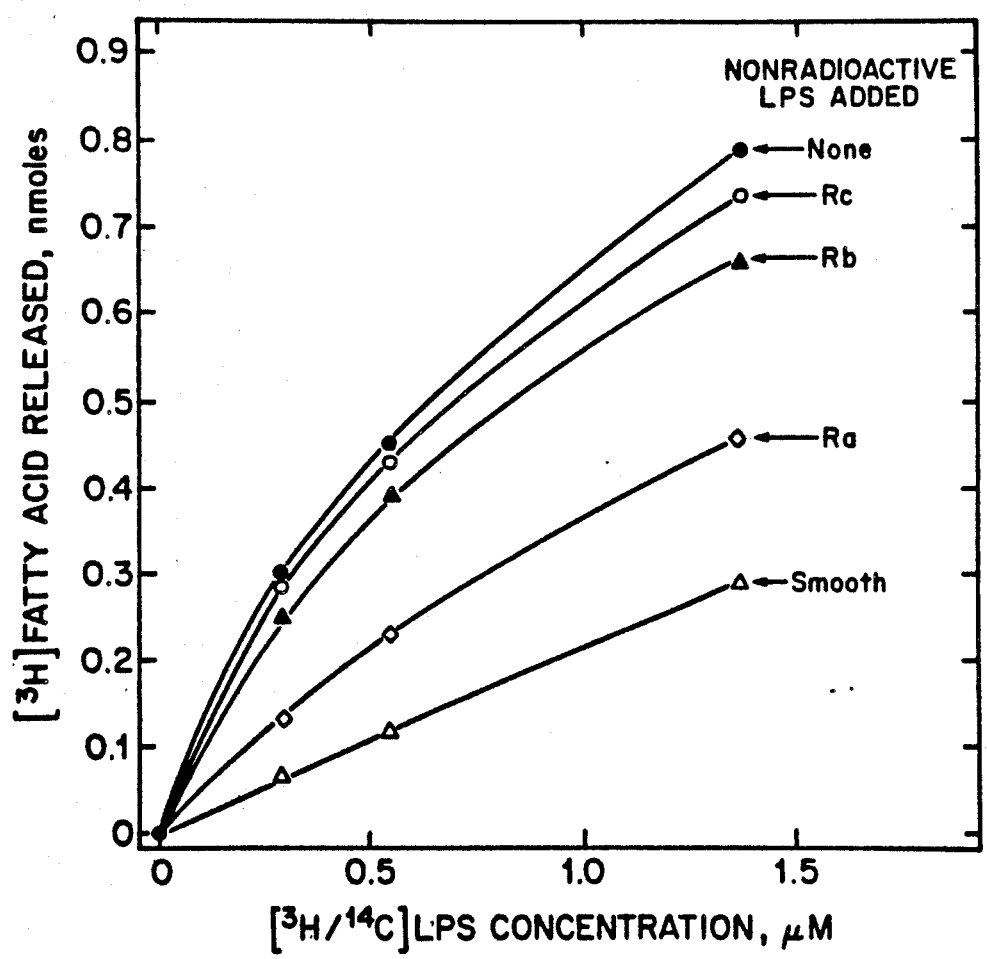

FIG. 5 shows the ability of nonradioactive LPS to diminish the release of $^3$H-fatty acids from the radiolabeled LPS substrate. Nonradioactive LPS from *S. minnesota* were added (adjusted to 0.27 umoles) to reaction mixtures that contained 0.27 umoles radiolabeled Rc-LPS. After incubation at 37° C. for 9 hours, the amount of released $^3$H-fatty acid was determined by extracting the fatty acids into chloroform and counting. The nonradioactive LPS had approximately 6 (Rc), 9 (Rb), 10 (Ra), and 14–50 (smooth) saccharides attached to lipid A.

DESCRIPTION OF THE PREFERRED EMBODIMENT

The present invention involves the use of a hydrolytic enzyme to detoxify bacterial lipopolysaccharide (LPS or endotoxin). This detoxification involves the hydrolysis of the ester bonds between nonhydroxylated acyl functions and the hydroxy groups of 3-hydroxymyristoyl (3-hydroxytetradecanoate) residues. These 3-hydroxymyristoyl functions are, in turn, bound in ester or amide linkage to a D-glycosaminyl disaccharide structure of the LPS lipid A moiety (see FIG. 2). The term acyloxyacyl hydrolase is used here to refer to this enzymatic activity.

An acyloxyacyl hydrolase was partially purified from cells of a human promyelocyte cell line, HL-60, and used to deacylate LPS from *S. typhimurium*. The enzymatically deacylated LPS lacked nonhydroxylated fatty acids but retained phosphate, 3-hydroxymyristoyl residues, and the polysaccharide chain. The effect of acyloxyacyl hydrolysis on the biological activities of the LPS was studied in several test systems. Loss of bioactivity in these assays was directly related to the degree of deacylation. Removal of approximately 95% of the non-hydroxylated fatty acids from the LPS had relatively minor impact on B-cell mitogenicity (5- to 12-fold loss of activity); intermediate effects on pyrogenicity, Limulus lysate clotting activity, and macrophage stimulation (10- to 20-fold loss of activity); and major impact on preparing the skin for the dermal Shwartzman reaction (greater than 100-fold loss of activity). The tissue toxicity of the LPS, measured in the Shwartzman reaction, was thus reduced at least 10-fold more than the immunostimulatory activity, measured in the B-cell mitogenicity assay.

These results generally agree with the reported roles of acyloxyacyl groups in the bioactivities of lipid A analogs. The presence of the hydrophilic LPS polysaccharide thus does not appear to alter greatly the influence that acyloxyacyl residues have in the biological activities of lipid A.

The discoveries comprising the present invention include the first description of an enzymatic activity that modifies the bioactivities of LPS. Acyloxyacyl hydrolase activity has been found in human neutrophils and mouse macrophages; the latter cells also contain mechanisms for removing 3-hydroxymyristate residues from LPS. Antibody-opsonized LPS undergo deacylation by both neutrophils and macrophages, so acyloxyacyl hydrolases should act on the LPS in phagocytosed bacteria as well. In addition to Salmonella LPS, the enzyme also deacylates LPS from *E. coli* and *Hemophilus influenzae* and *Neisseria meningitidis*. Acyloxyacyl hydrolases are most likely located in an acid intracellular compartment (lysosomes or endosomes), where deacylation of bacterial LPS would accompany the digestion of other bacterial components. Neutrophils are the front line of host defense against bacterial invasion, yet they are short-lived in tissue and also appear to regurgitate part of the material that they ingest; partially deacylated LPS, released from the neutrophils, may then interact with other host cells. It should be emphasized that the intracellular fate of LPS is not completely understood and that existing studies have all dealt with purified LPS, not the LPS in bacteria per se. Presently unknown deacylases, acyl transferases, or phosphatases may also process LPS intracellularly, with a variety of potential effects on LPS bioactivity.

The major role of acyloxyacyl hydrolases in animals may be to prevent LPS tissue toxicity. Remarkably, acyloxyacyl hydrolysis has a much smaller negative impact on the immunostimulatory potency of LPS, at least as measured by assays such as B-cell mitogenicity. Preservation of the immunostimulatory activities of LPS would allow animals to derive benefits such as immune priming during health and the enhancement of antibody formation during infections. In this regard it is interesting to consider that acyloxyacyl hydrolases may have a role similar to lysozyme, another enzyme of phagocytic cells that, as mentioned earlier herein, cleaves a toxic bacterial cell wall polymer (peptidoglycan) into products (muramyl peptides) that have immunostimulatory activities.

The present invention comprises the identification, characterization and purification of a human acyloxyacyl hydrolase. This acyloxyacyl hydrolase hydrolyzes the ester bonds between non-hydroxylated fatty acids and the 3-hydroxy functions of 3-hydroxy fatty acids bound in ester or amide linkages to glucosamine disaccharide of lipid A. Acyloxyacyl hydrolase action on LPS has effects upon both LPS toxicity and LPS immunostimulatory activity. LPS toxic effects are more greatly reduced by hydrolytic release of non-hydroxylated fatty acids than are the immunostimulatory effects. The ester or amide bonds between LPS glycosaminyl residues and the carboxylate of the 3-hydroxy fatty acids appears entirely or at least substantially unaffected by acyloxyacyl hydrolase.

Thus, the acyloxyacyl hydrolase may be administered as a therapeutic agent to patients subject to septic shock, for example, due to infection by Gram-negative bacteria. The administration of therapeutically effective amounts of the human acyloxyacyl hydrolase should decrease the toxicity of the bacterial LPS while not abolishing potentially helpful LPS biogenic effects such as B lymphocyte stimulation or induction of prostaglandin release. A prophylactic use of this enzyme may be appropriate where septic shock is a distinct possibility. These uses may be by the usual modes of administration such as by injection into veins, arteries, or peritoneum.

The antigen structure of the polysaccharide regions of LPS is not altered by acyloxyacyl hydrolysis. Enzymatic detoxification of lipid A without destruction of immunostimulatory activity may thus produce non-toxic LPS vaccines; the adjuvanticity of the detoxified lipid A would help promote the formation of antibodies to the polysaccharide antigen(s). As noted above, such antibodies may protect animals from various Gram-negative diseases.

LPS that have been detoxified by acyloxyacyl hydrolase may also be used therapeutically to antagonize the toxic effects of LPS present in (or released from) infecting bacteria. Preliminary studies have shown that enzymically deacylated LPS inhibits the ability of native LPS to stimulate the expression by human endothelial cells of a neutrophil-adherence factor. The adherence of neutrophils to endothelial cells is thought to play a role in the toxic effects of LPS. In addition, a lipid A analog that structually resembles the product of acyloxyacyl hydrolysis has been shown capable of reversing endotoxic shock in mice and sheep (Clin. Res., V 34, p 518A, 1986). Detoxified LPS may be superior to lipid A analogs for this purpose since the hydrophilic LPS polysaccharide chain enhances the solubility of the molecules in aqueous envionments.

A further use of the enzyme may be to reduce the toxicity of LPS that may contaminate therapeutic liquid injectants. Adding acyloxyacyl hydrolase to the injectant and allowing the enzyme to enzymatically hydrolyze ester bonds will detoxify LPS contained therein.

The following examples are presented to illustrate preferred embodiments of aspects of the present invention but are not intended to limit the scope of the invention unless otherwise specifically so stated in the claims appended hereto.

EXAMPLE 1

Partial Purification of Lipid A Acyloxyacyl Hydrolase

Cell source.

HL-60 cells (American Type Culture Collection, Rockville, Md., (ATCC) strain CCL-240) were propagated in RPMI-1640 medium that contained 8% fetal bovine serum (Hyclone), 10 units/ml penicillin G, and 50 ug/ml streptomycin. Typically, cultures of 250 ml in 750 ml flasks (Falcon) were harvested after 4-5 days of growth at 37° C. in an atmosphere of 5% $CO_2$. Twenty flasks (5 L medium) yielded approximately $5 \times 10^9$ cells. The cells were collected by centrifugation ($500 \times g$, 10 min, 4° C.), washed once with PBS (10 mM sodium phosphate, 0.15M sodium chloride, pH 7.1), and resuspended in 10 ml relaxation buffer (100 mM KCl, 3 mM NaCl, 3.5 mM $MgCl_2$, and 10 mM HEPES, pH 7.4).

The cells were then disrupted using several strokes in a Dounce homogenizer, followed by centrifugation ($478 \times g$, 5 min, 4° C.) to pellet nuclei and unbroken cells. The pellet was resuspended in 10 ml relaxation buffer and the homogenization-centrifugation was repeated. This cycle was continued (usually 4-5 times) until only approximately 5-10% of the cells were unbroken, as judged by microscopic examination of the pellet. The pooled supernatants from $5 \times 10^9$ cells typically contained 800-1000 mg protein.

Enzyme preparation.

Granules containing the enzyme were sedimented by centrifugation at $20,000 \times g$ for 10 min at 4° C. The supernatant was recentifuged and the combined pellets were resuspended in 27 ml relaxation buffer. Triton X-100 was added (0.5% vol/vol) and after sitting for 10 minutes in an ice bath, distilled water was added to the preparation to bring the volume to 30 ml (Triton X-100 concentration of 0.05%). Phenylmethylsulfonylfluoride (PMSF) and pepstatin were added (5 mM and 1 nM, respectively), and the preparation was centrifuged at $100,000 \times g$ for 60 min at 4° C. The pellet was discarded and the supernatant was frozen at $-20°$ C. With the exception of hydroxyapatite-chromatography, all purification steps were carried out at about 4° C.

Lentil lectin chromatography.

After another addition of PMSF and peptstatin, the 100K supernatant was diluted 2-fold in lectin column buffer (25 mM NaCl, 10 mM MES, pH 6.0, 0.01% Triton X-100) and applied to a (0.9 cm $\times$ 15 cm) column of lentil lectin-Sepharose 4B (Pharmacia). The column was washed sequentially with 15 ml volumes of 10 mM MES, pH 6.0, 0.01% Triton X-100, that contained (1) 0.025M NaCl, (2) 0.15M NaCl with 0.5M alpha-methyl mannoside, and (3) 0.5M NaCl with 0.5M alpha-methyl mannoside. The entire protein peak that eluted from the column was collected and concentrated, after adding further PMSF and pepstatin, in a 65 ml concentrating cell (Amicon) using an XM-50 filter. The concentrated glycoprotein peak could be frozen at $-20°$ C. without substantial loss of activity.

Cation exchange chromatography.

The glycoprotein concentrate was dialyzed overnight against 0.025M sodium acetate, pH 5.0, 0.02% (vol/vol) sodium azide, 0.05% Triton X-100, 2% taurine, and then for 1-2 hours against monoS start buffer (0.15M sodium acetate, pH 4.5, 0.05% Triton X-100, 0.02% sodium azide, 2% taurine). The precipitate that formed was sedimented ($10,000 \times g$, 10 min, 4° C.) and washed once with monoS start buffer. The combined supernatants were pooled and applied to a monoS column (Pharmacia) through a 0.22 um filter. Using the FPLC system (Pharmacia), proteins were eluted from the column using monoS start buffer with a gradient of 0-1.0M NaCl. The peak of enzymatic activity eluted at a NaCl concentration of 0.25M. Glycerol (20% vol/vol) was added to the peak fractions before they were pooled and concentrated using a Centricon-30 centrifugation device (Amicon).

Hydroxylapatite chromatography.

The concentrated fractions (0.5 ml) were diluted 10-fold with HPT buffer (0.02M sodium phosphate, pH 7.1, 0.02% sodium azide, 0.01% Triton X-100) and applied to a 1.0 $\times$ 3.0 cm column of hydroxylapatite (Biorad HPT). Proteins were eluted with a gradient of 0.02 to 0.4M sodium phosphate in the same buffer at room temperature. The peak of enzymatic activity eluted at a phosphate concentration of 0.2M. Glycerol (30%) was added and the fractions that contained the enzyme were pooled and concentrated as described above. The enzyme was stable at 4° C. for at least two months. The specific activity of the enzyme(s) in the hydroxylapatite peak fractions was 1000–1500 higher than in the post-nuclear homogenate.

Alternative cell source.

The above methods have also been used to purify acyloxyacyl hydolase from human peripheral blood neutrophils. The properties of the enzymatic activity obtained from the two sources are essentially identical. Because it can be obtained in larger quantities, the HL-60 cell enzyme has been used for the studies described in examples 2, 3, and 4.

EXAMPLE 2

Acyloxyacyl Hydrolase Activity upon LPS

Incubation conditions.

Biosynthetically radiolabeled LPS were prepared from *Salmonella typhimurium* grown in the presence of $^3$H-acetate and N-acetyl-1-[$^{14}$C]-glucosamine (incorporated into fatty acids and the glucosamine backbone, respectively, of the lipid A region). Acyloxyacyl hydrolysis was followed by measuring the release of $^3$H-fatty acids from the $^{14}$C-glycosamine-labeled LPS backbone.

Double-labeled quantities of ($^3$H/$^{14}$C) LPS (5 ug) were incubated at 37° C. with purified enzyme (10 ul) in a reaction mixture (0.5 ml) that contained 1 mg/ml fatty acid-free bovine serum albumin (BSA) (Sigma), St. Louis Mo.), 5 mM CaCl$_2$, 0.5% (vol/vol) Triton X-100, and 20 mM Tris-citrate, pH 4.8. The reaction was stopped at the desired time points by precipitating the LPS and BSA with 1.2 ml 95% ethanol. The precipitate was collected by centrifugation (12,000×g, 10 min, 4° C.) and washed once with 1.0 ml 80% ethanol. The precipitates were suspended in 0.5 ml normal saline and stored at −20° C. Aliquots of the precipitates and supernatants were counted and the percentage of each radiolabel that appeared in the supernatant was calculated. $^{32}$P-labeled *S. typhimurium* Rc LPS, prepared by growing strain PRX20 in a low phosphate medium that contained $^{32}$PO$_4$ (orthophosphate, New England Nuclear, Boston, Mass.), were incubated in parallel and precipitated in the same way; $^{32}$PO$_4$, when incubated in parallel and processed identically, was completely recovered in the ethanol supernatant.

Fatty Acid Analysis.

LPS were deacylated and precipitated with ethanol, and the ethanol-water supernatant was dried under N$_2$. The $^3$H-fatty acids were extracted into chloroform/methanol (2/1). Unincubated LPS and the deacylated LPS in the ethanol precipitate were hydrolyzed and the liberated fatty acids were extracted into chloroform. Recovery of radioactivity at each step was greater than 85%. The samples were analyzed by one-dimensional TLC using Silica gel G plates (Analtech). The solvent system was petroleum ether/ether/acetic acid (70/30/1). The spots were scraped from the plate and counted (84–96% recovery of added radioactivity). Values reported are the means of duplicate determinations.

Deacylation of LPS.

The time course of the deacylation reaction is shown in FIG. 3. $^3$H-fatty acids were released from the LPS over time, while neither $^{14}$C nor $^{32}$P (present in $^{32}$P-labeled *S. typhimurium* LPS that was treated with enzyme in parallel with the $^3$H/$^{14}$C LPS) was released significantly. The reaction reached an apparent maximum when approximately 32% of the $^3$H-fatty acids were extracted from the LPS; since 35% of the $^3$H-counts in this preparation were in nonhydroxylated fatty acids (NFA), 32% deacylation was consistent with nearly complete removal of these residues. This conclusion was supported by analysis of the fatty acid composition of the substrate LPS and the reaction products; 65% of the $^3$H-fatty acid counts in the LPS were in 3-OH-14:0 and 35% were in NFA, whereas the deacylated fatty acids that were released from LPS were almost entirely (94%) nonhydroxylated and 95% of the fatty acids in the partially deacylated LPS were 3-OH-14:0.

As shown in FIG. 4, samples of acylated and deacylated LPS were solubilized in sample buffer and subjected to electrophoresis in polyacrylamide gel with sodium dodecyl sulfate (SDS-PAGE).

Enzymatic deacylation produced an increase in the migration of the LPS in SDS-PAGE, consistent with a reduction in the size of the molecules (FIG. 4). This increase in migration was less than was observed for LPS that had been treated with alkali, which removes all four of the ester-linked fatty acids from lipid A (compare lanes 5 and 6, 9 and 10). Preservation of the original ladder pattern (which reflected the presence of molecules with different numbers of O-repeat units in the deacylated smooth LPS (lanes 1 and 2) indicated that the polysaccharide chain was not removed by enzymatic treatment.

Taken together, the evidence shows that the only modification in the enzymatically treated molecules was the loss of NFA.

EXAMPLE 3

Characteristics of Acyloxyacyl Hydrolase from Human Neutrophils

Enzymatic activity was approximately 1000- to 1500-fold increased in the hydroxylapatite peak fraction relative to the post-nuclear homogenate. The enzymatic activity was abolished by heating for 10 min at 80° C. but was not inhibited by EDTA (10 mM), PMSF (5 mM), pepstatin (1 mM), 2-mercaptoethanol (125 mM), para-hydroxymercuribenzoate (0.2 mM), sodium fluoride (50 mM), TPCK (0.1 mM), TLCK (0.1 mM), or soybean trypsin inhibitor (10 ug/ml). Calcium chloride (5–10 mM) and Triton X-100 (0.5% vol/vol) were required for maximal activity. Sodium deoxycholate inhibited the reaction. On gel filtration chromatography, the enzymatic activity eluted as a single peak with an approximate size of 50,000 to 70,000 daltons. The prior exposure of the preparation to Triton X-100 may artifactually influence this molecular weight estimate. The enzyme preparation did not contain phosphatases that acted on either *S. typhimurium* Rc-LPS or on a deep-rough *E. coli* LPS. Analysis of the enzyme hydrolysis product by thin-layer chromatography of the fatty acids showed that nonhydroxylated fatty acids were released from the LPS, whereas 3-hydroxymyristate residues were retained. Electrophoresis of the substrate and product on sodium dodecylsulfate polyacrylamide gel electrophoresis showed that the polysaccharide chain was not cleaved by the enzyme preparation. The data thus indicated that acyloxyacyl hydrolysis was the only effect of the enzyme preparation on the substrate LPS.

Nonradioactive LPS will compete with the radiolabeled LPS substrate. The longer the polysaccharide chain in the nonradioactive LPS, the better the competition (FIG. 5). In other experiments, when LPS with different polysaccharide chain lengths were radiolabeled and used as substrates for the enzyme, the shortest-chain LPS (Re) underwent significantly less hydrolysis than did the longer-chain LPS (Smooth, Rc). Thus acyloxyacyl hydrolase was more active in vitro on LPS substrates with long polysaccharide chains.

In experiments performed in collaboration with Dr. Gloria Sando, University of Iowa, a series of samples that contained increasing amounts of acyloxyacyl hydolase activity was found to have decreasing amounts of activity toward methylumbiliferyl oleate, a substrate for the enzyme acid lipase. Additionally, it was reported that acyloxyacyl hydrolase did not show hydrolytic activity toward cholesterol esters, glycerol trioleate, or toward dipalmitoylphosphatidylcholine, further distinguishing acyloxyacyl hydrolase from more common hydrolytic enzymes.

EXAMPLE 4

Alteration by Acyloxyacyl Hydrolase of LPS Bioactivities

R-LPS (rough LPS with short polysaccharide chain) from *S. typhimurium* was treated with acyloxyacyl hydrolase purified as described herein.

The deacylation of LPS was performed by incubating constant amounts of R-LPS and acyloxyacyl hydrolase for different time periods to produce different degrees of deacylation. Background deacylation (LPS incubated without enzyme) of 0.5-2.2% was subtracted from each value. Controls in each bioactivity assay included the reaction mixture and the reaction mixture that contained enzyme but no LPS; these controls were always negative.

The effects of acyloxyacyl hydrolysis on the bioactivities of the LPS were examined in five assays. The dermal Shwartzman reaction and the rabbit pyrogen test were used to measure in vivo toxicity. The mouse spleen cell (B-lymphocyte) mitogenicity assay and the stimulation of murine macrophages to release prostaglandins were used to measure potentially helpful bioactivity.

A dermal Shwartzman reaction was performed by intradermal injection of 2.5 ug of LPS or enzymically deacylated LPS into New Zealand white rabbits. Twenty-two hours later, the animals were given an intravenous dose of R-LPS (2-4 ug/kg). The dermal lesions were scored 4 to 6 hours later by 2 persons not knowing the identity of the samples. The average results from two rabbits are presented in the second and third columns of table 1.

Thermal response index (TRI) for LPS preparations was determined by injecting a New Zealand white rabbit weighing 3-4 kg with an intravenous dose of 50 ng LPS. Temperature was monitored with a rectal probe and recorded every 10 min. The Thermal Response Index is the integrated product of the temperature above baseline (0° C.) and time (degree-hours). (Zimmer et al. (1981) Peptides, V 2, p 413) Each dose was tested in 3 or 4 rabbits.

The measurement of half-maximal B-cell proliferation was measured by first incubating LPS preparations with mouse spleen cells in 98-well microtiter plates as described by Wannemuehler et al. (1984) J. Immunol. V 133, p 299. After 24 hours, methyl-[$^3$H] thymidine (0.5 uCi) was added to each well. The amount of radioactivity incorporated into each cell culture was measured 18 hours later. Each LPS was tested in four 5-fold dilutions; probit analysis of the results indicated the amount of each preparation that produced half-maximal stimulation of B-cell proliferation. The maximal stimulation index ($^3$H-radioactivity in stimulated cells/$^3$H-radioactivity in unstimulated cells) in the two experiments shown in Table 1 was 30 and 29, respectively.

The fourth assay was the Limulus lysate test, an in vitro clotting assay for LPS. Limulus lysate clotting was measured using 50 ul lysate (Cape Cod Associates, Woods Hole, Mass.) that contained 0.8 mg/ml n-benzoyl-L-valyl-glycyl-L-arginine PNA (Vega Biochemicals, Tucson, Ariz.) and 50 ul test sample. After incubation for 55 min at 37° C., 0.7 ml 40% acetic acid was added to each tube and the absorbance at 405 nm was measured. The values shown were derived by applying the results of 10-fold dilutions of test samples to a standard curve that was constructed with Rc LPS, with normalization to a starting concentration of 10 ug/ml. Dilutions were performed in pyrogen-free water. Each value is the mean of duplicate determinations that differed by less than 10%. Similar results were obtained in two additional experiments.

The stimulation of murine macrophages to release prostaglandin $E_2$ was also used as an index of immunostimulatory activity. Thioglycollate-elicited C3H/HeN mouse macrophages were incubated with acylated and 29%-deacylated LPS for 40 hours at 37° C. as described by Munford and Hall (1985) Infection and Immunity, V 48, pp. 464-473. $PGE_2$ levels in the cell supernatants were measured by radioimmunoassay (Campbell et al. (1980) Hypertension, V 2, pp 472-476).

The effects of acyloxyacyl hydrolysis on the bioactivities of LPS in these assays were studied in two ways. First, the impact of maximal LPS deacylation (30-32% loss of $^3$H-fatty acids) was assessed in each bioassay. Second, the dose-response relationship (degree of deacylation vs. loss of bioactivity) was studied in three of the assays.

Impact of Maximal Deacylation.

An intradermal injection of LPS, when followed 20 to 24 hours later by an intravenous injection of LPS, produces hemorrhagic necrosis of the skin at the intradermal injection site (dermal Shwartzman reaction). Maximally deacylated LPS (32% loss of $^3$H-fatty acids) did not prepare the skin for the reaction at doses as high as 10 ug, whereas LPS that had been incubated in reaction mixture without enzyme produced hemorrhage (4-5 mm diameter) and induration at doses of 0.1 ug; the reduction in toxicity was thus 100-fold or greater. Determination of the actual end-point was precluded by the lack of sufficient enzyme to deacylate the required large amounts of LPS. Deacylated LPS were also substantially less pyrogenic in rabbits than fully acylated LPS. Intravenous doses of 62 ng/kg of acylated and 32%-deacylated LPS produced mean thermal response indices of 12.0±2.5 (S. D.) and 5.0±1.0, respectively, while the indices with 25 ng/kg doses were 8.5±1.9 and 2.8+1.1, respectively. Deacylation of 32% of the H-fatty acids was associated with approximately 20-fold loss of activity in the Limulus test, a 5- to 12-fold reduction in B-cell mitogenicity, and a 10- to 20-fold reduction in the release of $PGE_2$ (prostaglandin $E_2$) by thioglycollate-elicited murine macrophages. Taken together, these results indicated that maximally deacylated LPS were at least 10-fold less toxic (as measured in the dermal Shwartzman test) than they were immunostimulatory (as measured by the B-cell mitogenicity test). The other assays gave intermediate results.

Dose-response.

Table 1 shows the relationship between the degree of deacylation and the loss of bioactivity for three of the assays. In each assay, loss of activity was directly related to the degree of deacylation.

In summary, acyloxyacyl hydrolysis greatly reduced the tissue toxicity of LPS while preserving relatively more of the immunostimulatory activity. This conclusion was consistent with the results of experiments, discussed in Background, that used lipid A analogs to evaluate the stimulatory role of acyloxyacyl groups. Acyloxyacyl hydrolysis makes possible the detoxification of LPS from many different bacteria, including LPS with long polysaccharide chains. The reduction in bioactivity was directly related to the degree of deacylation (Table 1).

Changes may be made in the construction, operation and arrangement of the various elements, steps and procedures described herein without departing from the concept and scope of the invention as defined in the following claims.

TABLE 1

EFFECTS OF DEACYLATION ON LPS BIOACTIVITIES

| Deacylation of LPS[1] (%) | Dermal Shwartzman Reaction[2] (0–4+) | | Dose for half-maximal B-cell Proliferation[3] (ug/ml) | | Limulus lysate Activity[4] (ug/ml) |
|---|---|---|---|---|---|
| | Rabbit 1 | Rabbit 2 | Expt 1 | Expt 2 | |
| 0 | 3+ | 3+ | 0.024 | 0.016 | 6.7 |
| 11–15 | 4+ | 2+ | 0.055 | 0.08 | 4.6 |
| 20–22 | 2+ | 2+ | 0.087 | NT | 3.4 |
| 29 | 1+ | 0 | 0.100 | NT | 1.3 |
| 32 | 0 | 0 | 0.14 | 0.18 | 0.4 |

[1]($^3$H-fatty acids released/total $^3$H-fatty acids in LPS) × 100.
[2]Constant amounts (2.5 ug) of R-LPS that had undergone different degrees of deacylation were injected intradermally in New Zealand White rabbits. 0 = no reaction; 1+ = less than or equal to 4 mm hemorrhage; 2+ = 5–9 mm hemorrhage; 3+ = 10–15 mm hemorrhage; 4+ = greater than 15 mm hemorrhage.
[3]Single-cell suspensions of C3H/HeN mouse spleen were incubated with LPS in 96-well microtiter plates and incorporation of $^3$H methyl thymidine measured.
[4]Limulus lysate clotting was measured using 50 ul lysate that contained 0.8 mg/ml n-benzoyl-L-valyl-glycyl-L-arginine PNA and 50 ul test sample.

Figure 1:
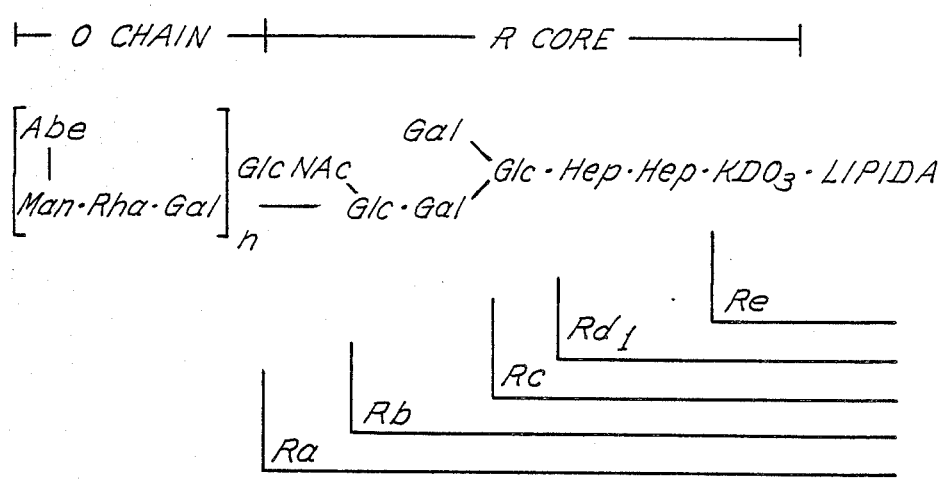
FIG. 1 shows the general structure of Salmonella LPS. The O-polysaccharide is connected to lipid A by the R-core region. n=0 to 50+. The structures of several R-core LPS are indicated.

What is claimed is:

1. An altered Gram-negative bacterial lipopolysaccharide
   (1) with 3-hydroxyfatty acids having at least 90% unesterified 3-hydroxy functions and
   (2) having toxicity reduced to a greater extent than immunostimulatory activity when compared to the unaltered lipopolysaccharide shown in FIG. 1, wherein said 3-hydroxyfatty acids are covalently linked to glucosaminyl moieties of the lipopolysaccharide lipid A.;

2. An altered Gram-negative bacterial lipopolysaccharide produced by the hydrolytic action of an acyloxy-acyl hydrolase upon the lipopolysaccharide shown in FIG. 1 under conditions such that at least 90% of the nonhydroxylated fatty acids or 2-hydroxyfatty acids bound in ester linkage to hydroxyl functions of 3-hydroxyfatty acids are removed and the resulting altered lipopolysaccharide has toxicity reduced to a greater extent than immunostimulatory activity when compared to the unaltered lipopolysaccharide.

3. The altered lipopolysaccharide of claim 1 or 2 defined further as being derived from Escherichia, Salmonella, or Hemophilus lipopolysaccharide.

4. A method of producing lipopolysaccharide altered so that toxicity has been reduced more than has immunostimulatory activity, the method comprising enzymatically hydrolyzing the ester linkage between fatty acids and the hydroxyl group of 3-hydroxyfatty acids bound in ester or amide linkage to lipopolysaccharide glycosaminyl residues.

5. A method of detoxifying a lipopolysaccharide-containing therapeutic liquid injectant, the method comprising treating the injectant by addition of acyloxyacyl hydrolase and allowing the acyloxyacyl hydrolase to enzymatically hydrolyze ester bonds.

6. A method of detoxifying a lipopolysaccharide-containing therapeutic liquid injectant, the method comprising enzymatically hydrolyzing the ester linkage between fatty acids and the hydroxyl group of 3-hydroxyfatty acids bound in ester or amide linkage to lipopolysaccharide glucosaminyl residues.

7. A method of vaccinating an animal to prevent Gram-negative bacterial diseases or treating animals with Gram-negative bacterial diseases, the method consisting essentially of administering to said animal a lipopolysaccharide altered by hydrolysis of at least 80% of ester linkages between fatty acids and hydroxy groups of 3-hydroxy fatty acids bound in ester or amide linkage to glucosaminyl lipopolysaccharide moieties.

8. The method of claim 7 wherein the administering is by intravenous, intraarterial, intraperitoneal or intramuscular injection.

9. A method for prophylactically treating an animal to prevent a particular Gram-negative bacterial disease, the method consisting essentially of vaccinating said animal, in an amount sufficient to produce immunity, with a lipopolysaccharide obtained from the particular Gram-negative bacterium and modified by hydrolysis of at least 80% of ester linkages between fatty acids and hydroxyl groups of 3-hydroxy fatty acids bound to glucosaminyl moieties of the lipopolysaccharide.

10. A method for prophylactically treating an animal to prevent a given Gram-negative bacterial disease, the method consisting essentially of vaccinating said animal with an amount sufficient to produce immunity of a lipopolysaccharide obtained from a Gram-negative bacterium of a type causing said given disease, and enzymatically altered to have 3-hydroxy fatty acids with at least 80% unesterified 3-hydroxy functions.

11. A method for prophylactically treating an animal to prevent a given Gram-negative bacterial disease, the method consisting essentially of administering to said animal an amount sufficient to produce immunity of a lipopolysaccharide obtained from a Gram-negative bacterium of a type causing said given disease, and enzymatically altered to have 3-hydroxy fatty acids with at least 80% unesterified 3-hydroxy functions, said administering inducing production by the animal of antibodies to O-polysaccharide or R-core antigens.

12. A method for treating an animal with a given Gram-negative bacterial sepsis, the method comprising administering to said animal a therapeutically effective amount of lipopolysaccharide obtained from a Gram-negative bacterium of a type causing said given disease, and enzymatically altered to have 3-hydroxy fatty acids with at least 80% unesterified 3-hydroxy functions, said amount being sufficient to block endogenously produced lipopolysaccharide at sites where said endogenously produced lipopolysaccharide exerts toxic effects.

13. The method of claim 9, 10, 11 or 12 wherein the altered lipopolysaccharide is obtained from Escherichia, Salmonella, or Hemophilus lipopolysaccharide.

14. The method of claim 9, 10, 11 or 12 wherein the altered lipopolysaccharide lacks at least 80% of nonhydroxylated fatty acids but retains phosphate, 3-hydroxymyristoyl residues and a polysaccharide chain characteristic of lipopolysaccharide.

* * * * *